United States Patent
Chau et al.

(10) Patent No.: US 8,355,134 B2
(45) Date of Patent: Jan. 15, 2013

(54) LOCALIZED PLASMON RESONANCE SENSING DEVICE AND FIBER OPTIC STRUCTURE

(75) Inventors: La-Kwan Chau, Chiayi (TW); Wei-Te Wu, Taichung (TW); Tzu-Chien Tsao, Yonghe (TW); Chien-Hsing Chen, Sanchong (TW); Wan-Yun Li, Miaoli County (TW)

(73) Assignee: National Chung Cheng University, Chiya-Yi (TW)

( * ) Notice: Subject to any disclaimer, the term of this patent is extended or adjusted under 35 U.S.C. 154(b) by 388 days.

(21) Appl. No.: 12/798,056

(22) Filed: Mar. 29, 2010

(65) Prior Publication Data

US 2011/0069316 A1 Mar. 24, 2011

(30) Foreign Application Priority Data

Sep. 22, 2009 (TW) .............................. 98131991 A

(51) Int. Cl.
*G01N 21/55* (2006.01)
*G02B 6/02* (2006.01)

(52) U.S. Cl. ........................................ 356/445; 385/123

(58) Field of Classification Search .......... 356/445–448, 356/300–301; 428/323, 403; 435/288.7, 435/7.1, 7.2; 436/501–503; 422/68.1, 50; 385/123

See application file for complete search history.

(56) References Cited

U.S. PATENT DOCUMENTS

| | | | |
|---|---|---|---|
| 5,864,397 A * | 1/1999 | Vo-Dinh ........................ 356/301 |
| 6,331,276 B1 * | 12/2001 | Takei et al. ................. 422/82.09 |
| 6,623,977 B1 * | 9/2003 | Farquharson et al. ......... 436/164 |
| 7,369,725 B2 * | 5/2008 | Takatori et al. .................. 385/39 |
| 8,072,606 B2 * | 12/2011 | Chau et al. ..................... 356/445 |
| 8,149,410 B2 * | 4/2012 | Isaka et al. ..................... 356/445 |
| 2004/0183176 A1 * | 9/2004 | Naya et al. ..................... 257/680 |
| 2005/0203495 A1 * | 9/2005 | Malak ............................... 606/9 |
| 2006/0263243 A1 * | 11/2006 | Hakari et al. ..................... 422/57 |
| 2007/0109544 A1 * | 5/2007 | Chau et al. ..................... 356/445 |
| 2008/0297800 A1 * | 12/2008 | Yamada et al. ................. 356/442 |
| 2009/0169866 A1 * | 7/2009 | Ostafin et al. .................. 428/323 |
| 2009/0203118 A1 * | 8/2009 | Kao et al. ..................... 435/288.7 |
| 2009/0273779 A1 * | 11/2009 | Baumberg et al. ............. 356/301 |

OTHER PUBLICATIONS

Wu, Wei-Te, et al., U-shaped Fiber Optics Fabricated with a Femtosecond Laser . . . , DTIP of MEMS & MOEMS, Apr. 1-3, 2009 Rome, Italy, EDA Publishing/DTIP.

* cited by examiner

*Primary Examiner* — Sang Nguyen
(74) *Attorney, Agent, or Firm* — Hudak, Shunk & Farine Co. LPA

(57) ABSTRACT

The present invention discloses a localized plasmon resonance sensing device and a fiber optic structure. The device comprises an optical fiber and a noble metal nanoparticle layer. The optical fiber has a plurality of notches, and such notches are located on the side surface of the optical fiber. The noble metal nanoparticle layer is located at the notch. As a result, when a light is launched into the optical fiber, a detecting unit can be used to detect a localized plasmon resonance signal which is generated by the interaction between the noble metal nanoparticle layer and the light.

10 Claims, 18 Drawing Sheets

LOCALIZED PLASMON RESONANCE SENSING DEVICE AND FIBER OPTIC STRUCTURE

BACKGROUND OF THE INVENTION

1. Field of the Invention

The present invention relates to a localized plasmon resonance sensing device and a fiber optic structure; in particular, the present invention relates to a localized plasmon resonance sensing device and a fiber optic structure with an array of sensing regions.

2. Description of Related Art

A fiber optic sensor basically uses an optical fiber to guide light waves generated by a light source to a test area, and variations regarding to certain physical or chemical quantity in the test area, e.g., stress, strain, temperature, refraction index, molecular concentration, may cause changes in the characters of the light wave, therefore through analyses on such changes of light wave characters, it is possible to infer such variations regarding to the physical or chemical quantity. The sensor signal of the fiber optic sensor is barely subject to interferences from electromagnetic noises and magnetic fields when operated in a fiber optic mode, and other hazards in the local environment such as ionizing radiation can be effectively avoided as well; as such, it can be appropriately applied in hostile environments, like within a nuclear power plant. Additionally, one single optical fiber can be simultaneously used as a sensor and a signal transfer line, and the integral size of the fiber optic sensor is usually smaller than that of a conventional sensor together with the transfer line, so it is possible to be deployed in a region spatially tight or extremely challenging for reaching.

The fiber optic sensor employs light as the media for excitation and transmission, rather than usage of electric current or voltage, thus risks in electric shock can be avoided, and it is suitable for medical measurement applications. Fiber optic materials are corrosion-proof, well adapted for deep ocean engineering and applications in a chemically corrosive environment, and provide good biocompatibility as well. The glass optical fiber demonstrates better temperature tolerance than the metal strain gauge, whose long-term stability and fatigue lifecycle are both higher than the resistive stain gauge, accordingly fitting for surveillances in long duration of time. Since the optical fiber is originally applied in the field of long distance communication, relevant technologies in fiber optic sensor can be conveniently exploited from technologies in long distance telemetry. Furthermore, wavelength division multiplexing technology developed in optical communication also facilitates multi-point telemetry with one single optical fiber, so the fiber optic sensor now has been comprehensively used in various fields such as aviation, medication, chemistry, geotechnical engineering, civil engineering and so forth.

Please refer first to FIG. 1, wherein a diagram illustrating the basic structure of an optical fiber is shown. The optical fiber in essence is an optical waveguide of an axially symmetric cylindrical structure, and, radially from the axle to the outside, can be divided into three layers, respectively the core 11, the cladding 12 and the jacket 13. The core 11 and the cladding 12 are basic elements for light transfer in the optical fiber and core 11 has a higher refractive index than that of cladding 12. The jacket 13 acts as the protection layer against external environment.

The well-known principle of the fiber optic sensor is, for example, to measure a certain physical (chemical) quantity, it first relates one characteristic of light to the variation of such a physical (chemical) quantity, next performs measurements on the result caused by such a variation, then the magnitude of the physical (chemical) quantity to be measured can be indirectly inferred. Regarding to an example of measurement on a physical quantity, if it is now to measure the torsion of a piece of mechanical part, bending the optical fiber leads to escape of light energy from the core and energy loss, and higher torsion results in more significant light energy loss; in other words, light energy is subject to the variation of torsion. Accordingly, by placing the optical fiber optic onto the mechanical part, it is possible to measure the intensity of transmitted light through the optical fiber, indirectly inferring the torsion of the mechanical part sensed by the optical fiber; on the other hand, for an example of chemical value measurement, a gas can absorb light of a certain specific wavelength and the absorption is proportional to the concentration of the gas. Therefore, an appropriate light is guided by the optical fiber to the test area so as to allow part of the light to interact with the gas in the test area, and get analyzed at the other end of the optical fiber by the spectrum thereof for measurement of intensity attenuation at the particular light wavelength such that it is possible to infer the concentration of the gas. Herein the modulation of light characteristic accountable for the variation of the physical (chemical) quantity may occur inside the optical fiber optic or at the exterior of the optical fiber as well; modulation of different characteristics of light may be measured individually or interactively, wherein the modulation mechanism may comprise:

1. absorption modulation;
2. chromatic dispersion modulation;
3. scattering based modulation;
4. luminescence-fluorescence based modulation;
5. refractive index based modulation;
6. geometric effect based modulation;
7. interferometric and phase modulation;
8. wavelength modulation; and
9. Doppler's effect modulation.

In addition, according the location where the sensing modulation occurs, different modulation mechanisms can be categorized as three major types: (1) extrinsic type, (2) intrinsic type, and (3) evanescent type characterized between the aforementioned two types. For the extrinsic typed sensor, it means that light, after guided to the test area through the optical fiber, momentarily leaves the optical fiber and is modulated by the external environment, then coupled into the original optical fiber or another optical fiber, and transferred to a signal generator for signal interpretation, wherein the optical fiber acts simply as a signal transmission line without participating in sensing operations; in the intrinsic typed sensor, on the other hand, light wave basically remains in the optical fiber all the time, and modulation from external environment cause changes in the internal characteristics of the optical fiber, thereby affecting a certain feature of the light wave (e.g., wavelength); the evanescent sensor uses changes of light energy loss in the evanescent field of the optical fiber caused by modulation from external environment to determine the environmental parameter to be detected; although such type of sensor may similarly involve in part of the light energy leaving the fiber core like the extrinsic typed sensor, a difference exists in that the modulation mechanism acts inside the cladding of the optical fiber, and the optical fiber is not only used as a signal transmission line but a sensing component as well.

To meet the requirements on sensing operations, the desktop Fiber Optic-Localized Plasmon Resonance (FO-LPR) sensing platform and implanted FO-LPR sensing system are developed. The implanted FO-LPR sensing system can be used to directly measure variations of specific biological molecules inside a living body, then the optical fiber of a suitable size can be selected based on the size of the object (e.g., organ or tissue) subject to the implantation. For example, if the optical fiber having a core of larger size is applied to a small animal, or to some small organs or tissues in a human body, such a larger size fiber may undesirably cause damages to a certain extent to the living body itself during implantation; serious damage may jeopardize its life while minor damage can result in additional metabolites or inflammation reactions in the living body, thus interfering the results originally intended to be measured.

SUMMARY OF THE INVENTION

In view of the aforementioned problems in prior art, the objective of the present invention is to provide a localized plasmon resonance sensing device which uses the optical fiber of smaller size as a LPR sensing component, wherein one possible choice thereof is the optical fiber commonly used in the field of communication in that both the core material and the cladding layer for such type of optical fiber is usually silica and the jacket layer is a polymeric material.

According to the objective of the present invention, a localized plasmon resonance sensing device is provided wherein a notch is created on the optical fiber as a sensing region, and the depth of the notch can be controlled so as to produce a shallower one by merely removing some parts of the jacket layer, while to produce a deeper one by exposing the core of the optical fiber and even removing part of the core. Various machining technologies can be employed for implementing the notched optical fiber, such as ultra-short pulse high energy laser processing technology, grinding fabrication technology or etching method and the like.

According to the objective of the present invention, a localized plasmon resonance sensing device is provided which comprises an optical fiber and a noble metal nanoparticle layer, wherein the noble metal nanoparticle layer consists of a plurality of noble metal nanoparticles on a surface, and the noble metal nanoparticles are substantially separated from each adjacent noble metal nanoparticles such that the absolute surface coverage is less than the closest-packed monolayer coverage and the conductivity of the noble metal nanoparticle layer is smaller than that of a metal film. The optical fiber comprises a plurality of notches, and such notches are located on the side surface of the optical fiber. The notch includes a first sidewall, a second sidewall and a bottom, wherein the bottom is located in parallel with the axle of the optical fiber, and the first sidewall and the second sidewall are connected to the bottom. The noble metal nanoparticle layer is located at the notch. As a result, when a light is launched into the optical fiber, a detecting unit is used to detect a localized plasmon resonance signal which is generated by the interaction between the noble metal nanoparticle layer and the excitation light. When the local refractive index around a nanoparticle is changed, the absorption and scattering cross-sections of the nanoparticle will change. As a result of such an interaction, the emerging light from the optical fiber will show a change in light intensity.

As disclosed herein, the first sidewall and the second sidewall are perpendicular to the cross-section of the optical fiber.

As disclosed herein, the bottom is a plane, a nonplanar surface, or a combination of both.

As disclosed herein, the first sidewall and the second sidewall respectively form an included angle with the bottom.

As disclosed herein, the first sidewall, the second sidewall and the bottom are located in the same plane.

As disclosed herein, each bottom of the notches is parallel with each other.

As disclosed herein, each bottom of the notches is located on the same plane or in different plane.

As disclosed herein, each bottom of the notches form an included angle with each other.

The optical fiber comprises a plurality of notches when the first sidewall, the second sidewall and the bottom are located in the same plane.

As disclosed herein, the preferred diameter of the core is less than 500 microns (μm), and the more preferred diameter of the core is in a range of 4 to 200 μm.

According to the objective of the present invention, an alternative localized plasmon resonance sensing device which comprises an optical fiber and a noble metal nanoparticle layer is provided. The optical fiber comprises a plurality of notches, and such notches are located on the side surface of the optical fiber. The notch includes a first sidewall and a second sidewall, and the first sidewall and the second sidewall are connected at an intersection line and form an included angle. The plane cutting the intersection line and the core axis of the optical fiber is referred as the normal plane. The noble metal nanoparticle layer is located at the notch. As a result, when a light is launched into the optical fiber, a detecting unit is used to detect a localized plasmon resonance signal which is generated by the interaction between the noble metal nanoparticle layer and the excitation light.

As disclosed herein, the normal plane of each notch is formed by connecting the intersection line of the first sidewall and the second sidewall with the core axis of the optical fiber, and the normal planes are parallel.

As disclosed herein, the normal plane of each notch is formed by connecting the intersection line of the first sidewall and the second sidewall with the core axis of the optical fiber, and each normal plane forms an included angle with an adjacent normal plane.

As disclosed herein, each of the notches is provided thereon with the noble metal nanoparticle layer of different localized plasmon resonance band.

According to the objective of the present invention, a fiber optic structure is provided which comprises an optical fiber and a plurality of notches. The notches are located on the side surface of the optical fiber and each of the notches includes a first sidewall, a second sidewall and a bottom, wherein the bottom is located in parallel with the axle of the optical fiber, and the first sidewall and the second sidewall are connected to the bottom.

According to the objective of the present invention, a localized plasmon resonance sensing device is provided, wherein a notched structure is formed on the optical fiber, and a noble metal nanoparticle layer is modified onto the surface of the notch for localized plasmon resonance (LPR) detection of analytes. The above-mentioned noble metal nanoparticle layer is made of one of the sphere-shaped noble metal nanoparticle, the cube-shaped noble metal nanoparticle, the cone-shape noble metal nanoparticle, the bar-shaped noble metal nanoparticle and the shell-shaped noble metal nanoparticle, and the noble metal may be gold, silver or platinum. When a light is guided into the optical fiber, it interacts with the noble metal nanoparticles at the sensing region, thus generating the localized plasmon resonance effect, and the light signal modulated by such an effect can be used as the basis for detection.

Besides, the present invention further provides a localized plasmon resonance sensing device. Wherein, since a relationship exists between the optical properties of noble metal nanoparticles and their surrounding environment, the notched optical fiber according to the present invention, after modification of noble metal nanoparticles onto the surface of the core, is allowed to perform detection of analytes such as gaseous molecules and biological molecules based on the localized plasmon resonance effect; while suppose the notches are fabricated in a helical arrangement, the notched optical fiber itself may become a micro-mixer employed in a micro-fluidic chip. Hence, the notched optical fiber provided in the present embodiment offers multi-functional features and is beneficial to the analysis processes.

In summary of the aforementioned descriptions, the localized plasmon resonance sensing device and the fiber optic structure according to the present invention provides the following advantages:

(1) since the optical fiber for communication is used as the optical fiber for the present invention, both the core and cladding of the optical fiber is made of a silica material, the process to fabricate the sensing regions can be carried out by partially removing the cladding, thereby eliminating the problem of insufficient mechanical strength due to the complete removal of a certain length of the cladding; besides, abundant and inexpensive accessories for the communication optical fiber exist in the market;

(2) regarding the integration of the notched fiber optic sensor and the micro-fluid chip, since the notched optical fiber has a small size and can maintain the mechanical strength to a certain level, it is possible to significantly reduce the volume of sample for detection which allows to lower sensing operation cost and lessen the demand for hard-to-obtain biological sample;

(3) when having a special arrangement of a number of notches along the optical fiber, the notched optical fiber itself may generate disturbance in the fluid passing by the surface thereof which can preferably act as a mixer employed in a micro-fluidic channel. Hence, the notched optical fiber provided in the present embodiment offers a multi-functional feature and is beneficial to the analysis processes;

(4) the notched optical fiber according to the present invention is a small-sized optical fiber, e.g., the communication optical fiber, and is fabricated as the light wave guide sensing component;

(5) the notched fiber optic architecture according to the present invention simply partially remove the cladding of an optical fiber, thereby eliminating the problem of insufficient mechanical strength due to the complete removal of a certain length of the cladding; hence, facilitating implementation of the implanted FO-LPR system.

DETAILED DESCRIPTION OF THE PREFERRED EMBODIMENTS

Figure 1:
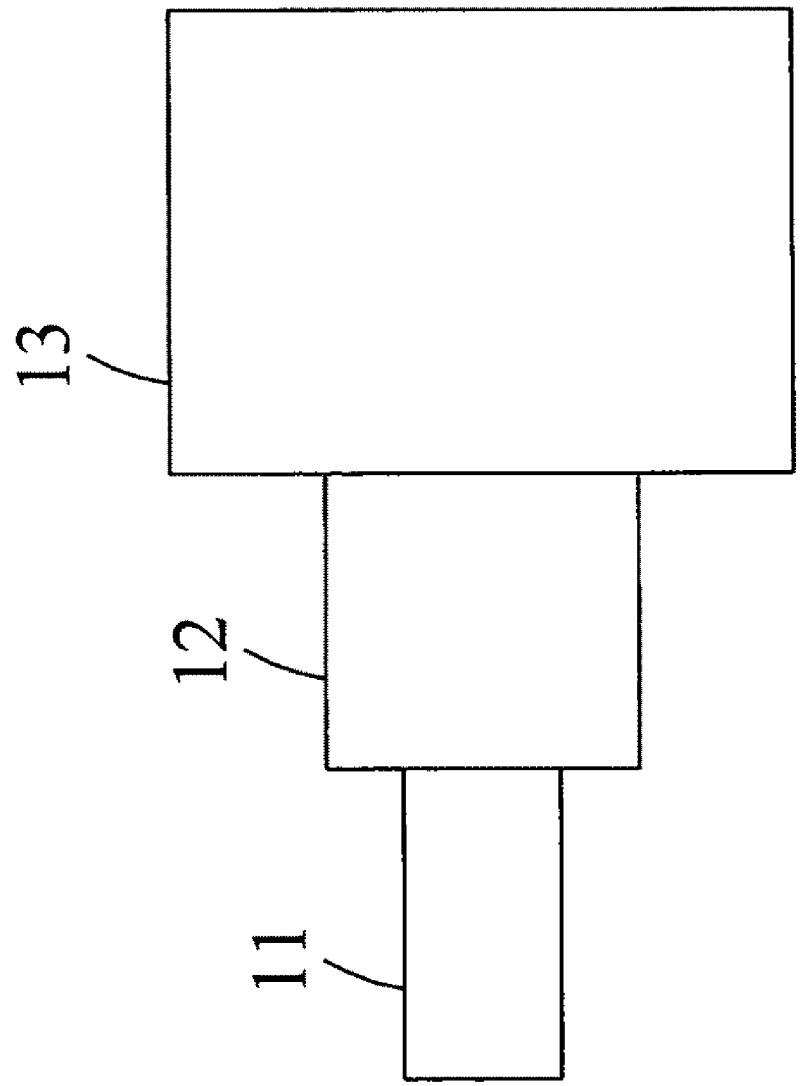
FIG. 1 is a diagram showing the basic structure of a prior art optical fiber.
Figure 2:
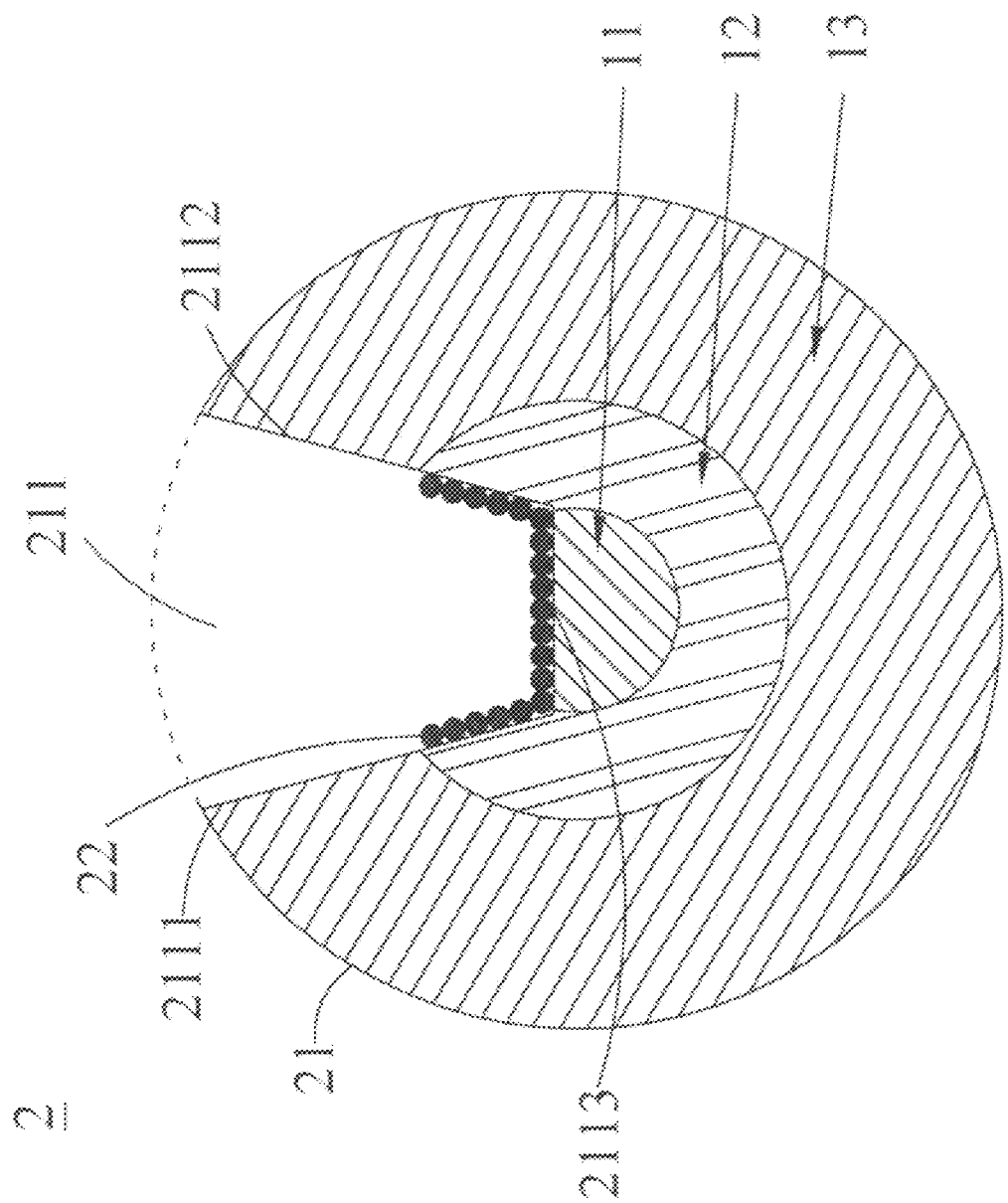
FIG. 2 is a diagram showing a first embodiment of the localized plasmon resonance sensing device according to the present invention.

Please refer first to FIG. 2, wherein a diagram for a first embodiment of the localized plasmon resonance sensing device according to the present invention is shown. Please refer then to FIG. 3, wherein a side view diagram showing the first embodiment of the localized plasmon resonance sensing device according to the present invention is shown. Please refer also to FIG. 4, wherein another side view diagram for the first embodiment of the localized plasmon resonance sensing device according to the present invention is shown. As shown in these diagrams, a localized plasmon resonance sensing device 2 comprises an optical fiber 21 and a noble metal nanoparticle layer 22. The optical fiber 211 may be a U-shaped optical fiber (also referred as U-fiber) comprising a plurality of notches 211, wherein the notches 211 are located on the side surface of the optical fiber 21; each of the notches 211 includes a first sidewall 2111, a second sidewall 2112 and a bottom 2113, wherein the bottom 2113 may be a plane, located in parallel with the axle of the optical fiber 21, and the first sidewall 2111 and the second sidewall 2112 are connected to the bottom 2113 such that the first sidewall 2111 and the second sidewall 2112 respectively form an included angle with the bottom 2113.

Figure 3:
FIG. 3 is a side view diagram showing the first embodiment of the localized plasmon resonance sensing device according to the present invention.
Figure 4:
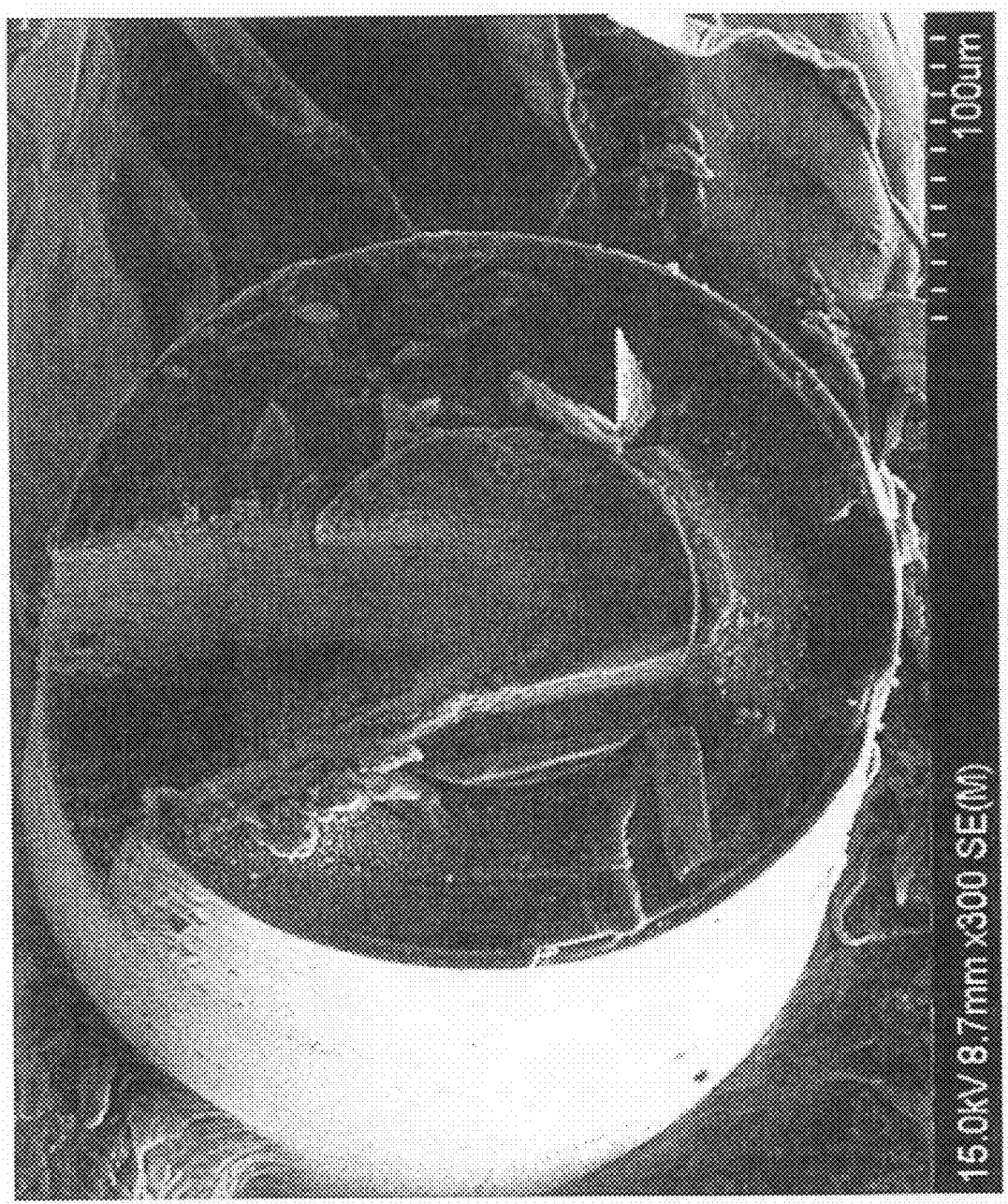
FIG. 4 is another side view diagram showing the first embodiment of the localized plasmon resonance sensing device according to the present invention.

The noble metal nanoparticle layer 22 is located at the notch 211 and may be composed of gold nanoparticles, silver nanoparticles or platinum nanoparticles. When a light enters into the optical fiber 21, the noble metal nanoparticle layer 22 interacts with the light to generate localized plasmon resonance. FIG. 3 illustrates a notched optical fiber without a jacket, while FIG. 4 depicts a notched optical fiber with a jacket. Both the optical fiber with or without the jacket can be used as the optical fiber 21 of the localized plasmon resonance sensing device 2. The optical fiber 21 used in the present invention includes a core whose diameter may be less than 500 μm, and the preferred range for the diameter of the core may be 4 to 200 μm.

Figure 5:
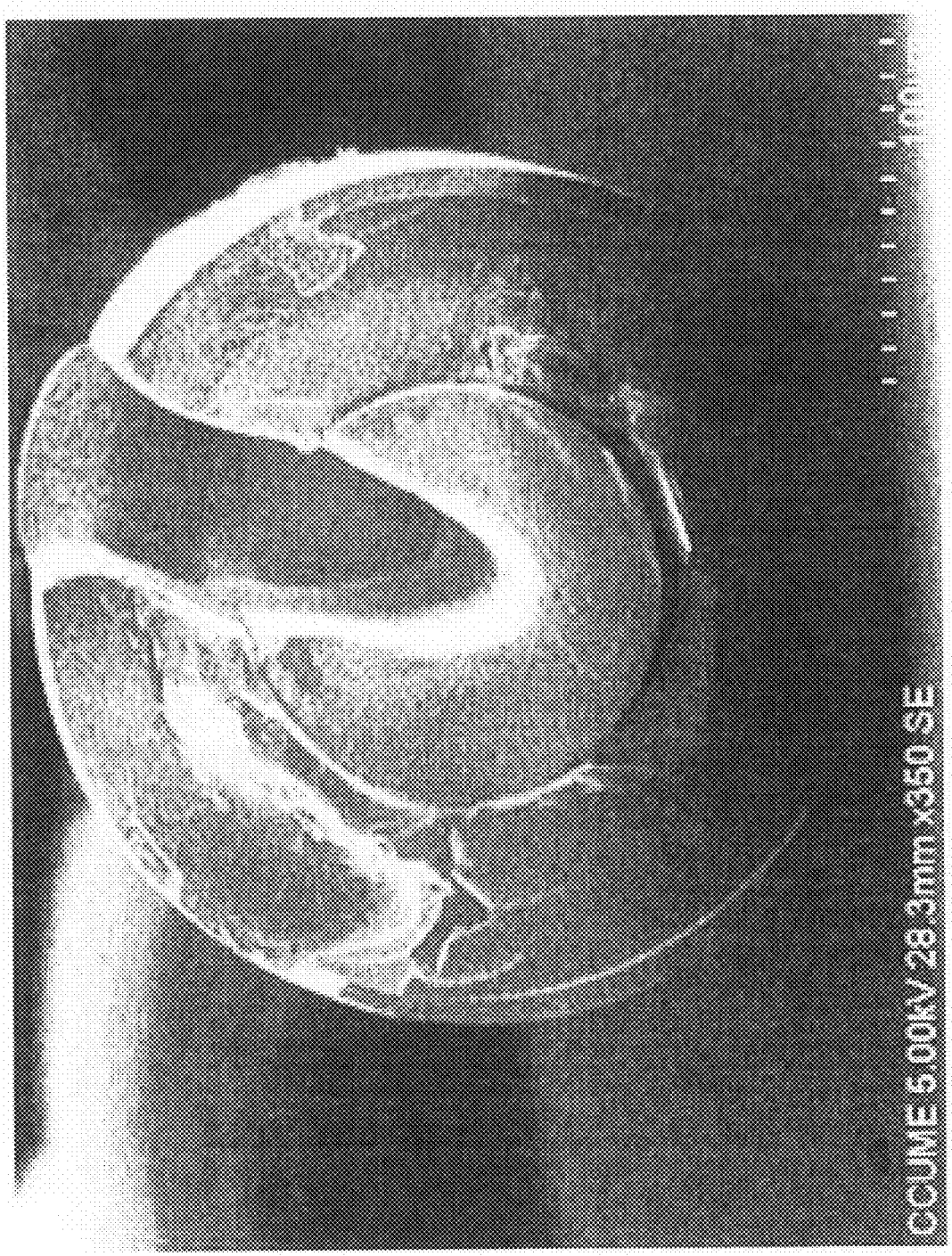
FIG. 5 is a diagram showing a second embodiment of the localized plasmon resonance sensing device according to the present invention.

Please refer next to FIG. 5, wherein a diagram for a second embodiment of the localized plasmon resonance sensing device according to the present invention is shown. In this Figure, the optical fiber may be an U-fiber comprising a plurality of notches located on the side surface of the optical fiber; the notch has a first sidewall, a second sidewall and a bottom, wherein the bottom is a nonplanar surface and located in parallel with the axle of the optical fiber, and the first sidewall and the second sidewall are connected to the bottom.

Figure 6:
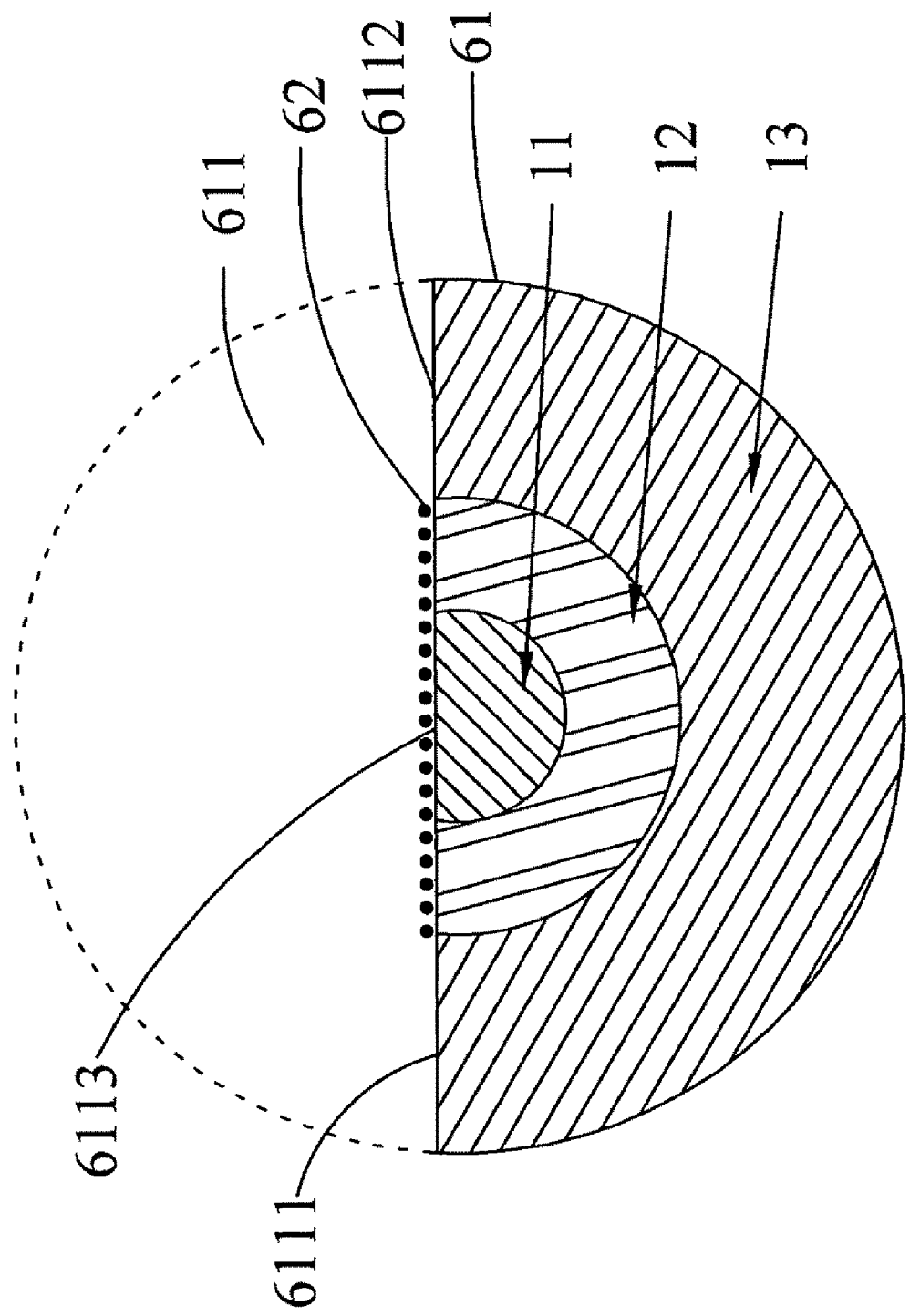
FIG. 6 is a diagram showing a third embodiment of the localized plasmon resonance sensing device according to the present invention.
Figure 7:
FIG. 7 is an SEM diagram showing the third embodiment of the localized plasmon resonance sensing device according to the present invention.

Subsequently, please refer to FIG. 6, wherein a diagram for a third embodiment of the localized plasmon resonance sensing device according to the present invention is shown. Please refer to FIG. 7 as well, wherein an SEM diagram for the third embodiment of the localized plasmon resonance sensing device according to the present invention is shown. In these diagrams, the localized plasmon resonance sensing device 6 comprises an optical fiber 61 and a noble metal nanoparticle layer 62. The optical fiber 61 comprises a plurality of notches 611, wherein the notches 611 are located on the side surface of the optical fiber 61, wherein when the first sidewall 6111, the second sidewall 6112 and the bottom 6113 of the notch 611 are located in the same plane, the optical fiber may be a D-shaped optical fiber (D-fiber). The noble metal nanoparticle layer 62 is located at the notch 611. In addition, the noble metal nanoparticle layer 62 may further comprise a recognition element (e.g., antibody, antigen, DNA, chemoreceptor, etc.) in order to sense a specific analyte.

Figure 8:
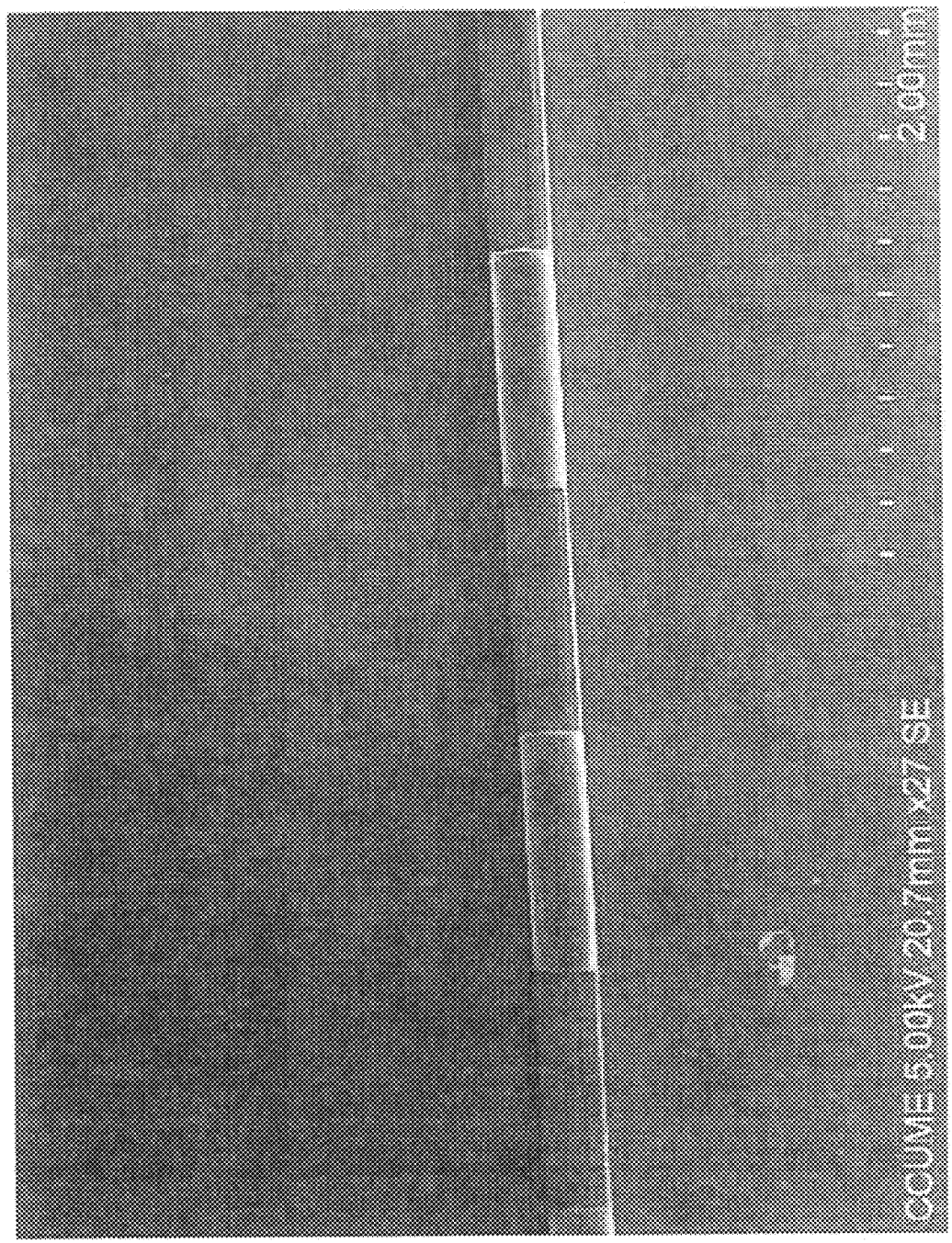
FIG. 8 is an SEM diagram showing a D-shaped single-phase multiple-notch optical fiber in a fourth embodiment of the localized plasmon resonance sensing device according to the present invention.

Please refer to FIG. 8, wherein an SEM diagram for a single-phase D-fiber in a fourth embodiment of the localized plasmon resonance sensing device according to the present invention is shown. In the diagram, multiple notches are located along the axle of the optical fiber, and the bottom of these notches may be located in the same plane. Such an arrangement of notches is referred to be in a fixed phase here. Since the bottom of each notch has a fixed phase, it may be also referred as a single-phase multiple-notch optical fiber; however, this represents simply one of many possible configurations. The optical fibers are all deemed as the effective configurations in accordance with the present invention so long as they have the notches located along the axle of the optical fiber.

Figure 9:
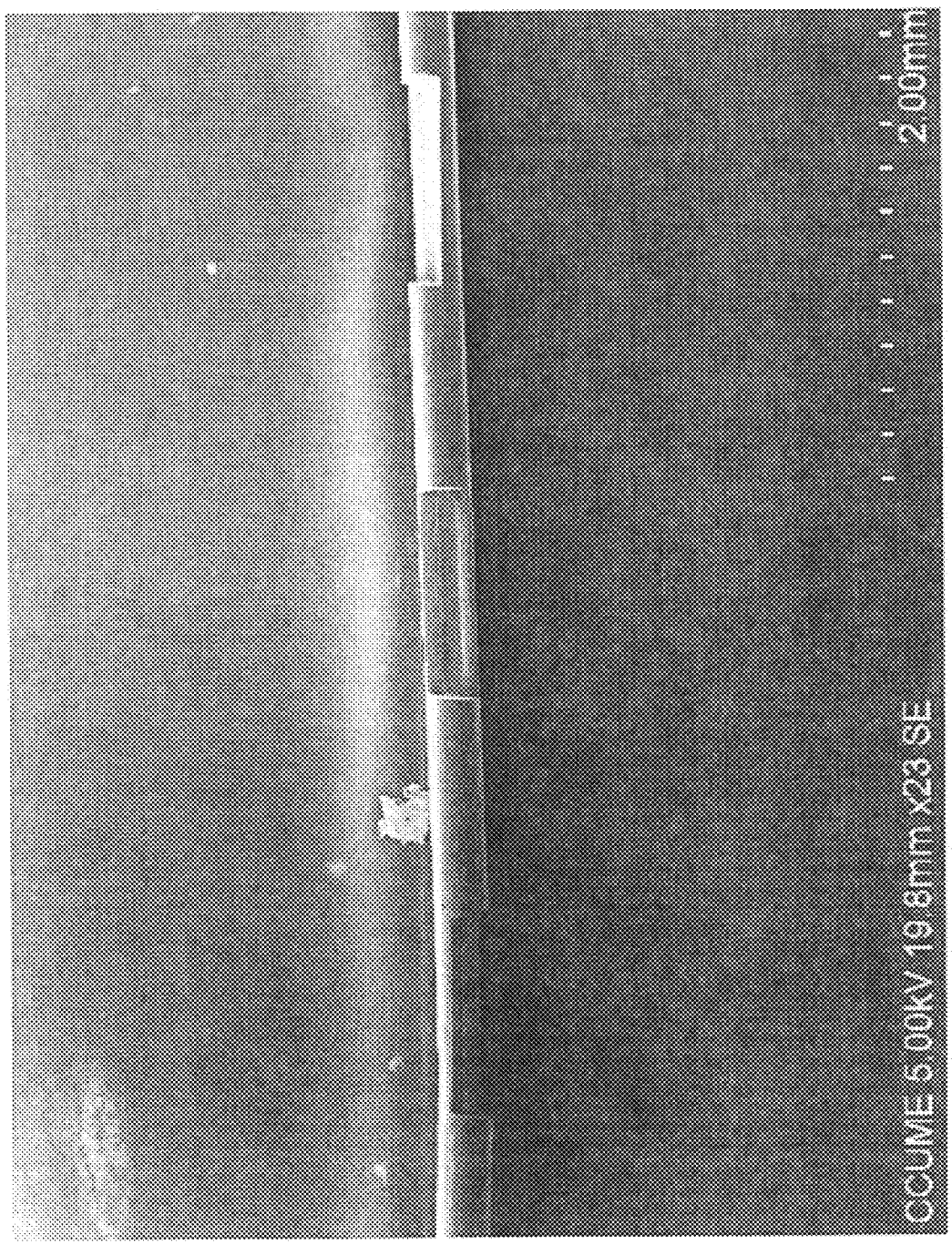
FIG. 9 is an SEM diagram showing a D-shaped multiple-phase multiple-notch optical fiber in a fifth embodiment of the localized plasmon resonance sensing device according to the present invention.

Please refer now to FIG. 9, wherein an SEM diagram for a multiple-phase D-fiber in a fifth embodiment of the localized plasmon resonance sensing device according to the present invention is shown. In the diagram, multiple notches are located along the axial line of the optical fiber and the bottom of these notches are not located in the same plane, referring to as in different phases; since the bottom of each notch has a different phase, it may be also referred as a multiple-phase multiple-notch optical fiber.

Figure 10A:
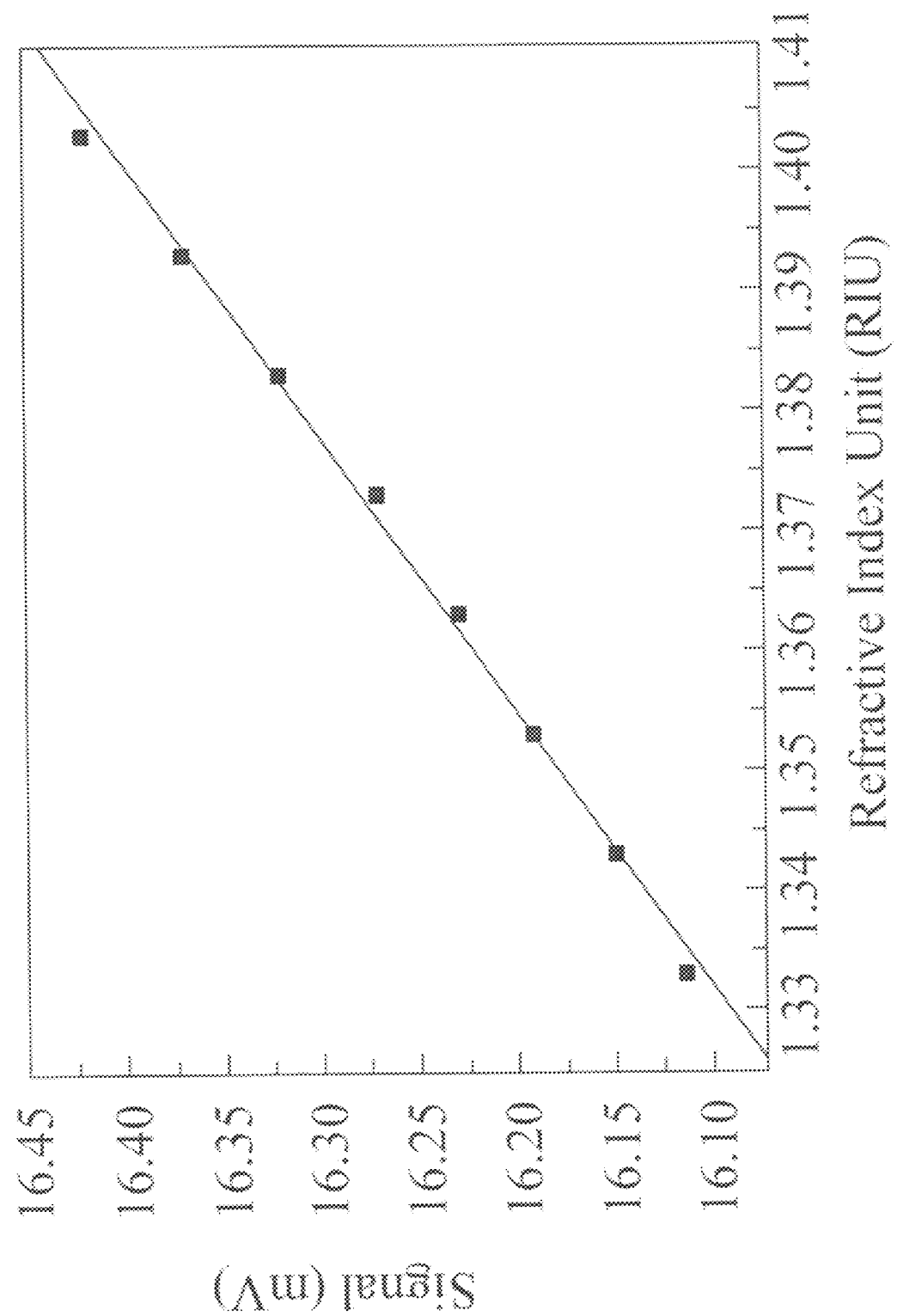
FIG. 10a is a diagram showing the relationship between the signal detected by the U-shaped fiber optic localized plasmon resonance sensing device and the refraction index of sucrose solution according to the present invention.
Figure 10B:
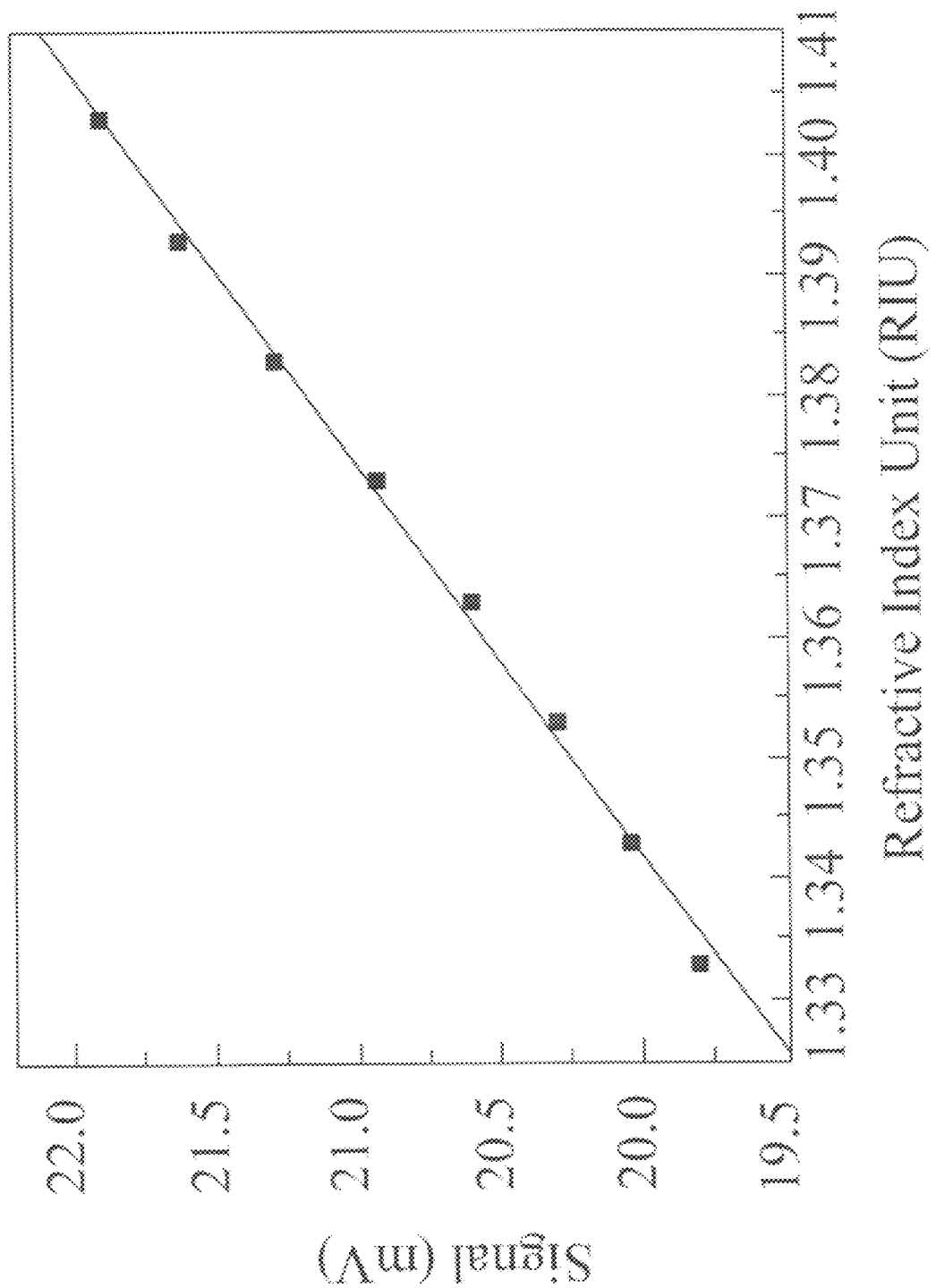
FIG. 10b is a diagram showing the relationship between the signal detected by the D-shaped fiber optic localized plasmon resonance sensing device and the refraction index of sucrose solution according to the present invention.

Please refer then to FIG. 10a, wherein a diagram of the relationship between the signal detected by the U-fiber localized plasmon resonance sensing device and the refraction index of sucrose solution according to the present invention is shown. Please refer also to FIG. 10b, wherein a diagram of the relationship between the signal detected by the D-fiber localized plasmon resonance sensing device and the refraction index of sucrose solution according to the present invention is shown. When a light enters into the optical fiber, a detecting unit is used to detect a localized plasmon resonance signal which is generated by the interaction between the noble metal nanoparticle layer and the light. When the adopted optical fiber is an U-fiber, the refractive index resolution of the sensing device on the refraction index of sucrose solution can reach $1.768 \times 10^{-3}$ RIU. In case a D-fiber is used as the sensing fiber, the refractive index resolution of the sensing device can reach $2.2 \times 10^{-4}$ RIU.

Figure 11:
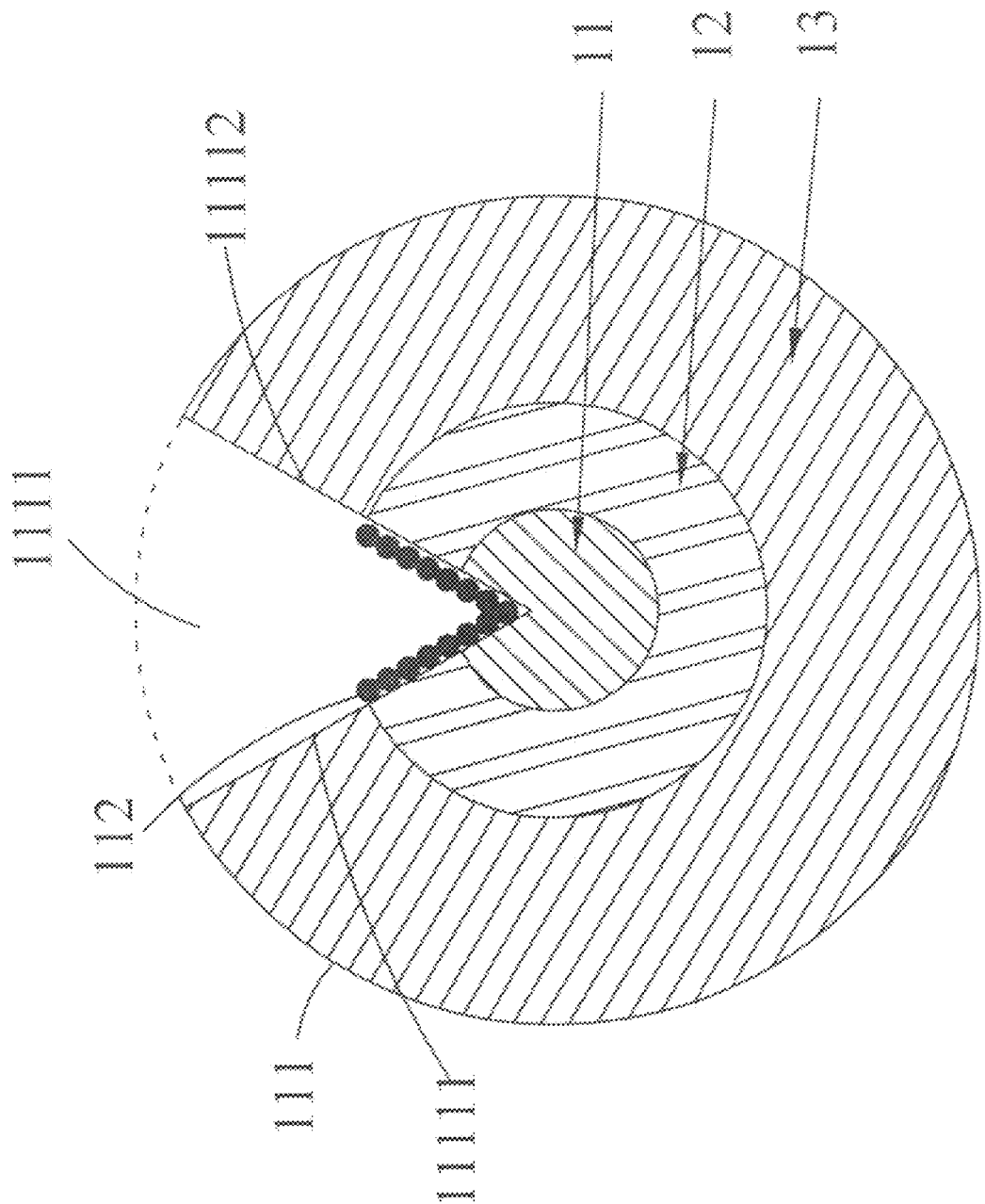
FIG. 11 is a diagram showing a sixth embodiment of the localized plasmon resonance sensing device according to the present invention.

Please refer to FIG. 11, wherein a diagram for a sixth embodiment of the localized plasmon resonance sensing device according to the present invention is shown. Please refer also to FIG. 12, wherein a side view diagram for the sixth embodiment of the localized plasmon resonance sensing device according to the present invention is shown. A localized plasmon resonance sensing device comprises an optical fiber 111 and a noble metal nanoparticle layer 112. The optical fiber 111 has a plurality of notches 1111, wherein the notches 1111 are located on the side surface of the optical fiber. The notches 1111 include a first sidewall 11111 and a second sidewall 11112, and the first sidewall 11111 and the second sidewall 11112 are connected at an included angle to form a V-shaped cross-section. The noble metal nanoparticle layer 112 is located on the sidewall of the notches 1111. When a light enters into the optical fiber 111, a detecting unit is used to detect a localized plasmon resonance signal which is generated by the interaction between the noble metal nanoparticle layer and the light. The notches 1111 may be in a single-phase configuration or a multiple-phase configuration, just like the configurations illustrated in the fourth embodiment and the fifth embodiment.

Figure 13:
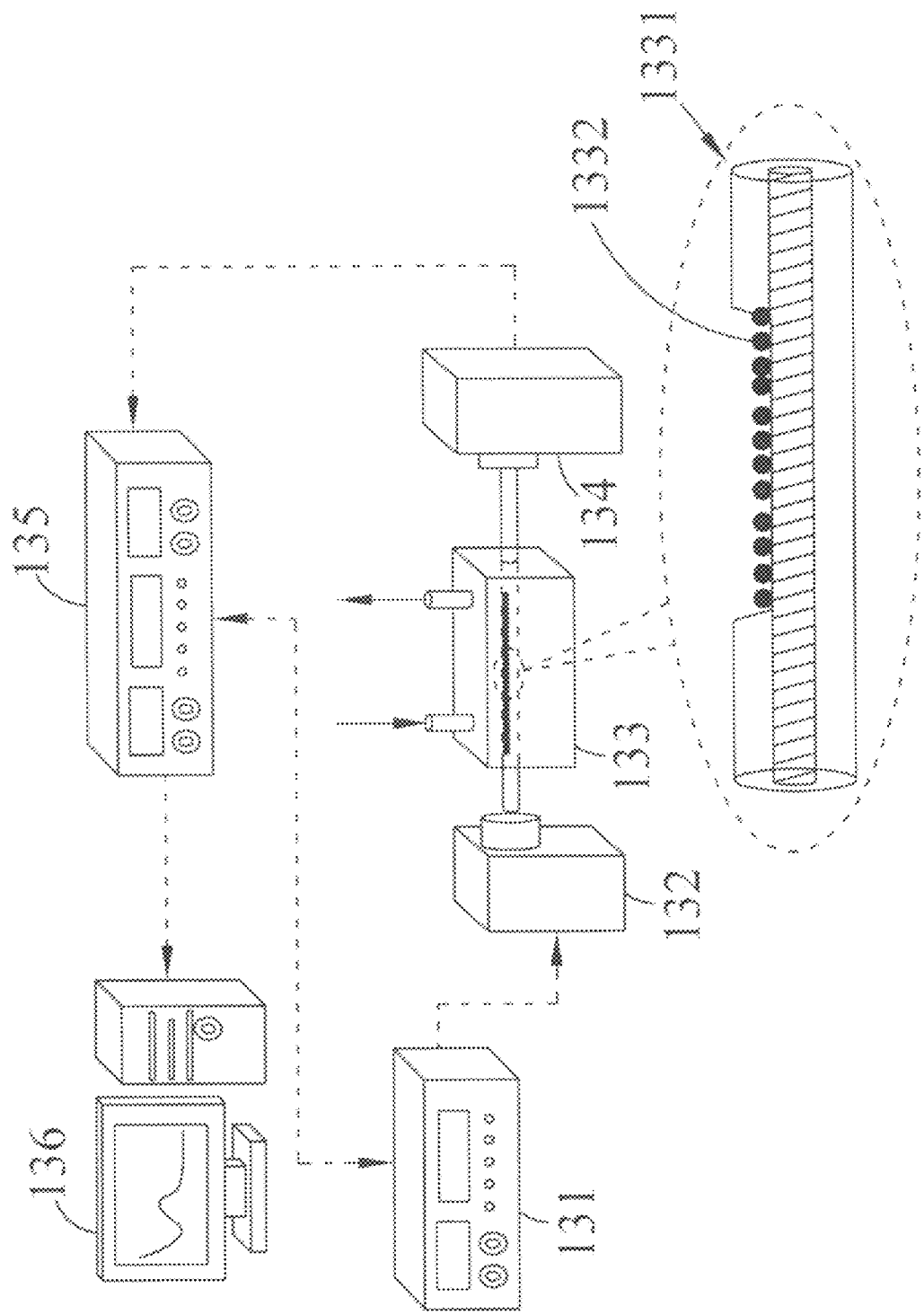
FIG. 13 is a diagram showing the localized plasmon resonance sensing system according to the present invention.

Please refer to FIG. 13, wherein a diagram for the localized plasmon resonance sensing system according to the present invention is shown. The surface of the core in the notched optical fiber 1331 processed by means of a femtosecond laser is modified with gold nanoparticles 1332, which can be used for biosensing based on the principle of the fiber optic localized plasmon resonance. In the illustrated system, an excitation signal is provided to a green light LED 132 by a function generator 131, and herein the green light LED 132 is used because its emission wavelength is approximately 530 nm which is relatively close to the peak value of absorption in spectrum by the gold nanoparticles of diameter 10~20 nm, so the use of such an LED 132 can offer a better LPR effect, thereby improving its sensitivity. Then, the light of the LED 132 is guided into the localized plasmon resonance sensing device 133 and a detecting unit 134 (e.g., photo diode) is placed at the end of the optical fiber to receive the emerging light signal; subsequently, the received light signal is converted into an electrical signal, and the converted electrical signal is transferred to a lock-in amplifier 135 for signal amplification and processing, and finally the signal is analyzed by a computer 136 for further analyzing and determining the detection result, thereby constructing a complete system.

The present embodiment employs the chemical reduction method to synthesize the sphere-shaped gold nanoparticles 1332 (AuNPs), wherein sodium citrate is used as the reducing agent and protective agent during reduction for the sphere-shaped gold nanoparticles 1332 in an aqueous phase environment. After completion of the chemical reaction, an ultraviolet/visible light (UV/Vis) spectroscopy is used to observe its optical characteristic absorption band and a transmission electron microscope (TEM) to review its shape, size and uniformity. As shown in the UV-Vis absorption spectrum, the characteristic absorption band is approximately located at 518 nm, the average particle diameter thereof is about 12~15 nm, and good consistencies in terms of shape and particle diameter uniformity are exhibited. Subsequently, the surface of an optical fiber is modified with the synthesized gold nanoparticles 1332 by using (poly(allylamine hydrochloride)) (PAH), wherein the PAN is a polymeric material with positive charge, modified onto the $SiO_2$ material (the core) by means of physical absorption, while the amino group ($NH_2$) exposed on the other side thereof may form a bonding with the gold nanoparticles, such that the synthesized gold nanoparticles 1332 are capable of being modified onto the surface of the core of the optical fiber 1331 for LPR detection.

Figure 12:
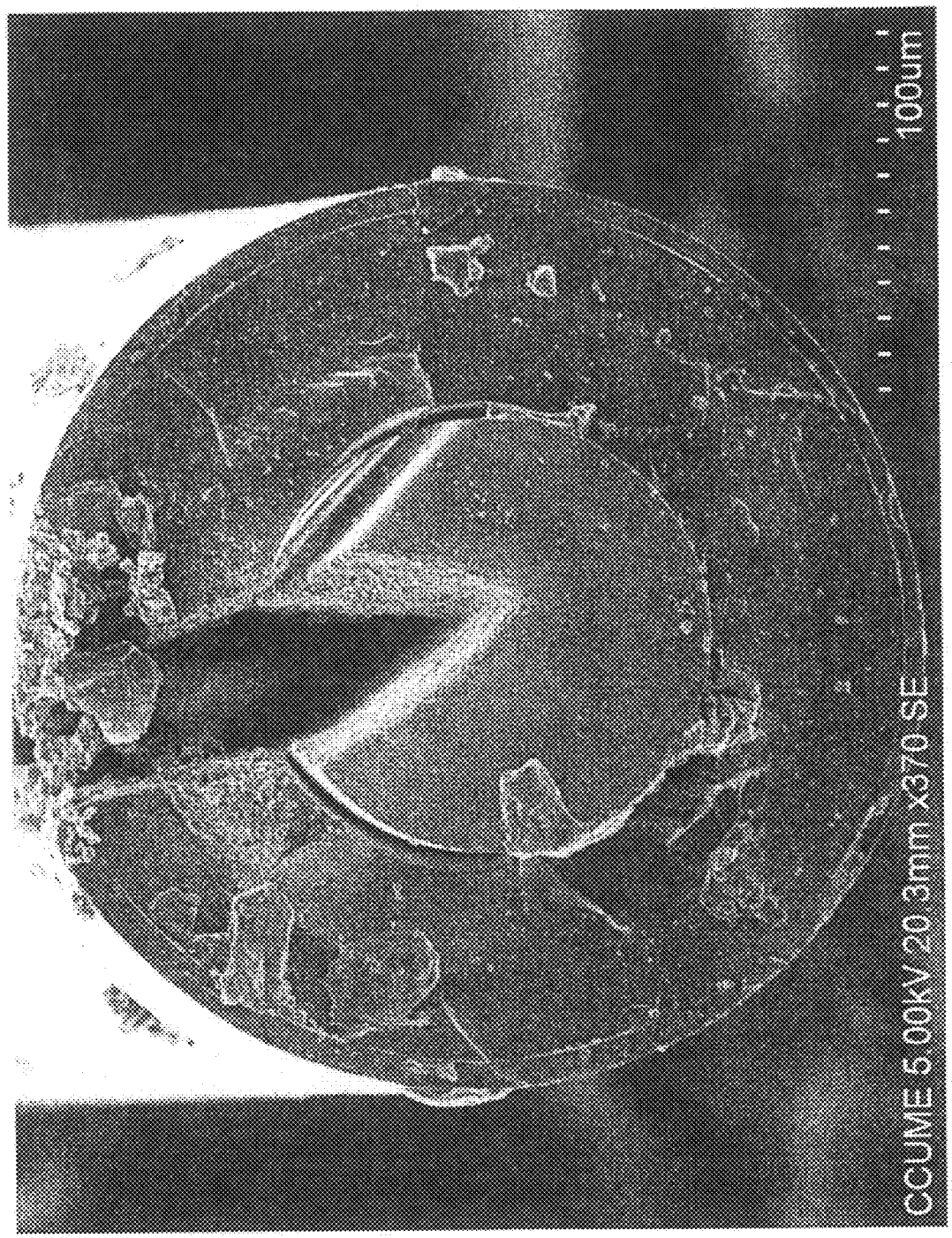
FIG. 12 is a side view diagram showing the sixth embodiment of the localized plasmon resonance sensing device according to the present invention.

In the optical detection by the notched optical fiber, the present embodiment is addressed to delve into the influence of refraction index on the light intensity outputted by the notched optical fiber 1331 modified with gold nanoparticles 1332 thereon, wherein the detection system is set up as shown in FIG. 12. Initially, the well-prepared sucrose solutions of seven different concentrations and deionized water are provided, wherein the concentrations of the sucrose solutions and deionized water as well as the corresponding refraction indices are illustrated as below in Table 1.

TABLE 1

Parameter Table of Aqueous Sucrose Solutions

| NO. | 1. | 2. | 3. | 4. |
|---|---|---|---|---|
| Concentration (wt %) | 0 | 0.068 | 0.1325 | 0.1949 |
| Refraction Index Unit (RIU) | 1.333 | 1.343 | 1.353 | 1.363 |

| NO. | 5. | 6. | 7. | 8. |
|---|---|---|---|---|
| Concentration (wt %) | 0.254 | 0.3105 | 0.3655 | 0.417 |
| Refraction Index Unit (RIU) | 1.373 | 1.383 | 1.393 | 1.403 |

During detections, the notched optical fiber modified with gold nanoparticles is placed into the channel and 1 ml of sucrose solution is injected at a rate of approximately 0.03 ml/s. After each injection, the output signal is recorded for roughly 10 minutes, and then next injection of sucrose solution is performed. The above process is repeated until all sucrose solutions marked No. 1~No. 8 are measured (wherein the item No. 1 represents deionized water), and the changes in light signal thereof per item is measured.

Figure 14:
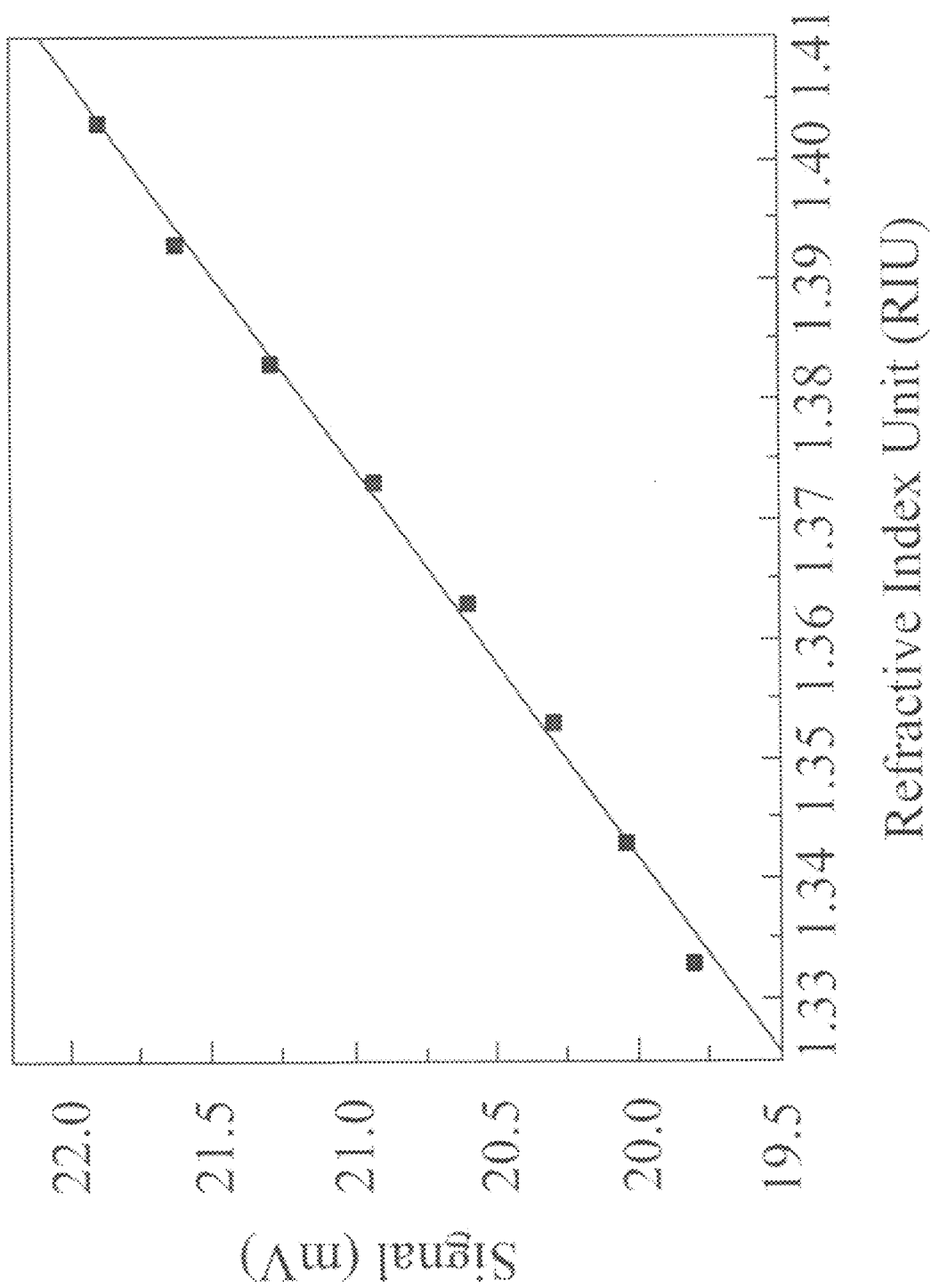
FIG. 14 is a diagram showing the relationship between the signal detected by the U-shaped fiber optic localized plasmon resonance sensing device and the refraction index refraction index of sucrose solution.

Please refer now to FIG. 14, wherein a diagram of the relationship between the signal detected by for of a notched optical fiber modified with gold nanoparticles and the refractive index of the solution is shown. It can be seen from the diagram that when the refractive index increases from 1.333 to 1.403, the light signal is roughly enhanced by 2.25 mV whose linearity is 0.9983 with a sensitivity of $2.2 \times 10^{-4}$ RIU.

Figure 15:
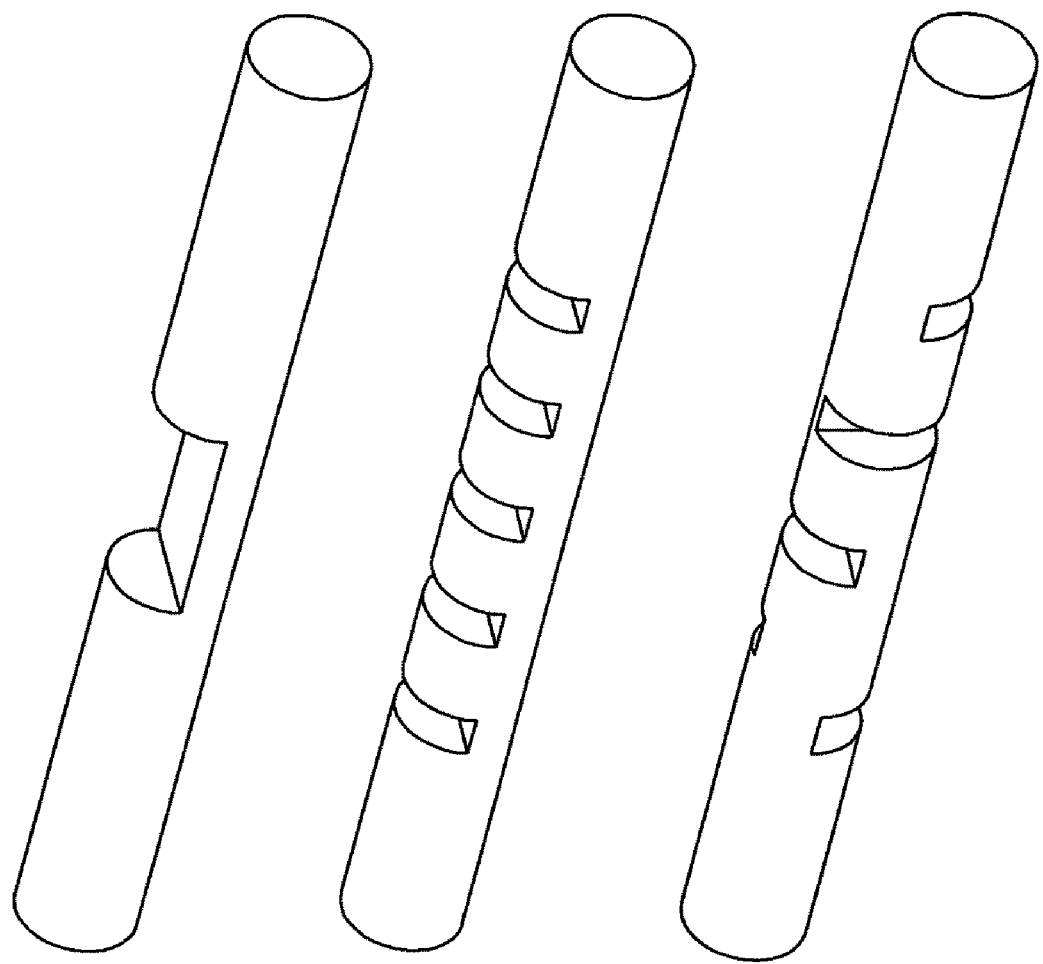
FIG. 15 is a diagram showing different forms of notched optical fiber according to the present invention.

Please refer to FIG. 15, wherein a diagram of the notched optical fiber according to the present invention is shown. When one single notch is formed, it can be considered as a single-notch optical fiber; while multiple notches are formed and each notch has the same phase, it can be considered as a single-phase multiple-notch optical fiber. In addition, if multiple notches are formed and each notch has a different phase, then it can be considered as a multiple-phase multiple-notch optical fiber. There exist various alternations and combinations relating to the structure of notched optical fiber, such as the aforementioned U-fiber, D-fiber or V-fiber etc., which can be applicable for the localized plasmon resonance sensing device according to the present invention in conjunction with appropriate modulations. The configuration for sidewalls may be taken as the cross-section parallel to the optical fiber, whereas other forms are also feasible. In case multiple notches are formed on the side surface of the optical fiber, it can be arranged either with a fixed phase or with multiple phases.

Figure 16A:
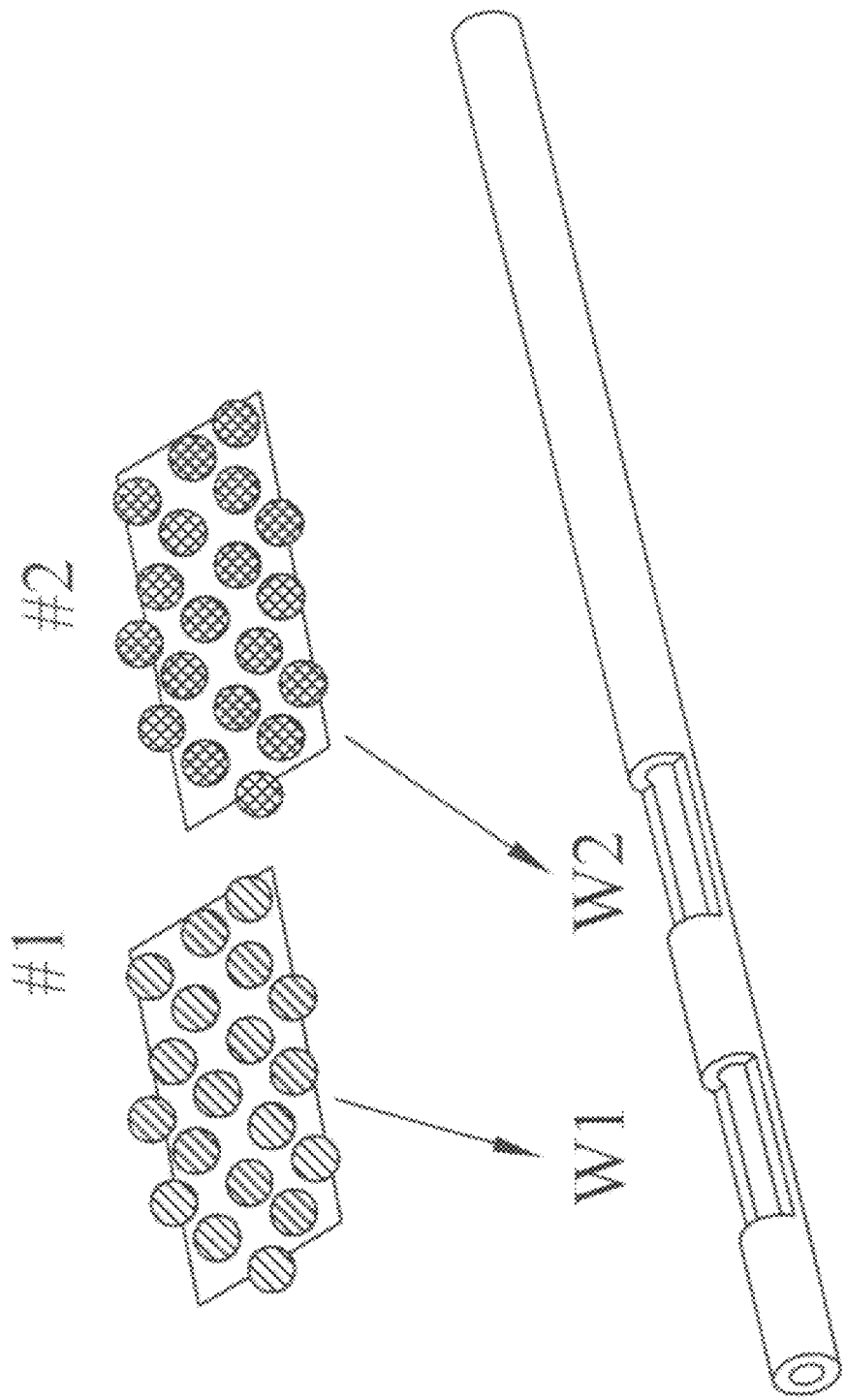
FIG. 16a is a diagram showing a seventh embodiment of the localized plasmon resonance sensing device according to the present invention.

Please refer now to FIG. 16*a*, wherein a diagram for a seventh embodiment of the localized plasmon resonance sensing device according to the present invention is shown. The sensing region marked as W1 can be used to sense the corresponding target material, and one example is implemented by modifying thereon the noble metal nanoparticle layer #1 that contain a recognition element; while the region marked as W2 is a reference region, one example is implemented by modifying thereon the noble metal nanoparticle layer #2 that does not contain a recognition element, such that its signal can be used to compensate refraction index changes in solution caused by environmental variations (e.g., temperature, high viscosity of samples); each of the noble metal nanoparticle layer #1 and the noble metal nanoparticle layer #2 has respective localized plasmon resonance bands, so such a plurality of sensing regions on the optical fiber may construct a fiber optic sensor enabling a self-compensatory feature.

Figure 16B:
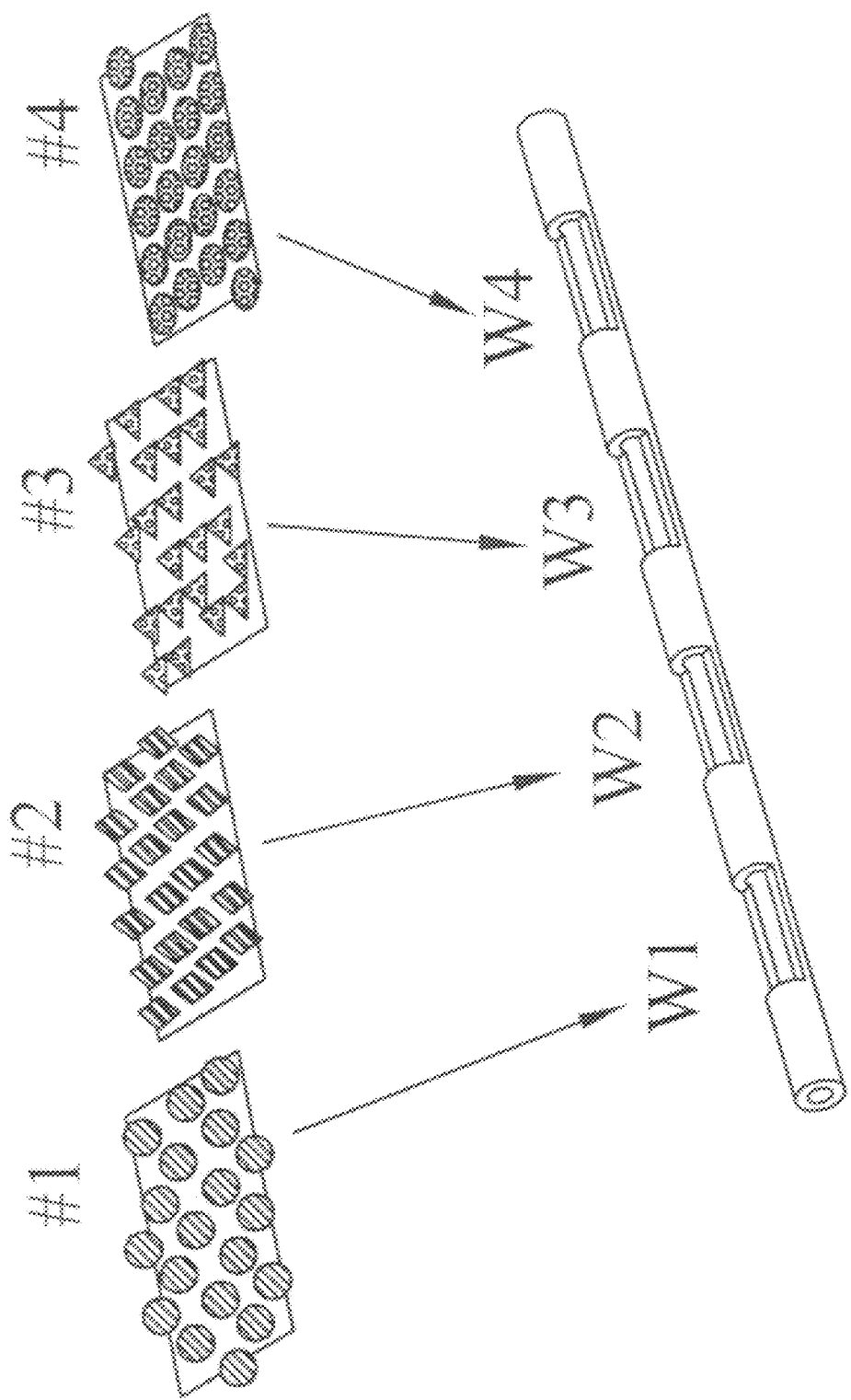
FIG. 16b is a diagram showing an eighth embodiment of the localized plasmon resonance sensing device according to the present invention.

Please refer finally to FIG. 16*b*, wherein a diagram for an eighth embodiment of the localized plasmon resonance sensing device according to the present invention is shown. W1, W2, W3 and W4 indicate different sensing regions (notches), so each notched optical fiber is able to detect different corresponding target materials in a sample, wherein one example is implemented by modifying different noble metal nanoparticle layers (e.g., gold, silver, platinum nanoparticle of different size, shape and so forth) respectively onto W1, W2, W3 and W4, wherein each noble metal nanoparticle layers exhibiting its specific localized plasmon resonance band, thus absorption peaks of different wavelengths may occur on the spectrum. Since each nanoparticle layer is respectively modified to contain a different recognition element thereon, each notched optical fiber can, through the signals generated at different wavelengths, sense the existence of different target materials in the sample.

Furthermore, the item W1 may be a reference region enabling a self-compensatory feature, while W2, W3 and W4 indicate sensing regions which may be modified with different noble metal nanoparticle layers #2, #3 and #4, and each noble metal nanoparticle layer is further modified to contain a different recognition element thereon; in this way, the plurality of sensing regions on the optical fiber allow to sense different corresponding target materials placed in the sample, accordingly forming a self-compensatory and multiplex fiber optic sensor. Various changes and combinations with suitable modulations for the structure of the notched optical fiber exist and the above-mentioned advantages and advancement are thus provided so as to allow the notched optical fiber to become an innovative niche-based fiber optic sensor.

The aforementioned descriptions are simply illustrative, rather than being limiting. All effectively equivalent modifications, alternations or substitutions made thereto without departing from the spirit and scope of the present invention are deemed to be encompassed by the claims set forth hereunder.

What is claimed is:

1. A localized plasmon resonance sensing device, comprising:

an optical fiber comprising a plurality of notches located on a side surface of the optical fiber, each of the notches comprising a first sidewall, a second sidewall and a bottom, the bottom being located in parallel with the axle of the optical fiber, and the first sidewall and the second sidewall being connected to the bottom; and a noble metal nanoparticle layer located at the plurality of notches, wherein each of the notches is provided thereon with the noble metal nanoparticle layer of different localized plasmon resonance band; wherein when a light is launched into the optical fiber, a detecting unit is used to detect a localized plasmon resonance signal which is generated by the interaction between the noble metal nanoparticle layer and the light.

2. The localized plasmon resonance sensing device according to claim 1, wherein the first sidewall and the second sidewall are perpendicular to the cross-section of the optical fiber.

3. The localized plasmon resonance sensing device according to claim 1, wherein the bottom is a plane, a nonplanar surface, or a combination thereof.

4. The localized plasmon resonance sensing device according to claim 1, wherein the first sidewall and the second sidewall respectively form an included angle with the bottom.

5. The localized plasmon resonance sensing device according to claim 1, wherein the first sidewall, the second sidewall and the bottom are located in the same plane.

6. The localized plasmon resonance sensing device according to claim 5, wherein the bottoms of the notches are located in the same plane.

7. The localized plasmon resonance sensing device according to claim 1, wherein the bottoms of the notches are located in different planes.

8. A localized plasmon resonance sensing device, comprising:

an optical fiber comprising a plurality of notches located on a side surface of the optical fiber, each of the notches comprising a first sidewall and a second sidewall, and the first sidewall and the second sidewall being connected at an included angle; and a noble metal nanoparticle layer located at the plurality of notches, wherein each of the notches is provided thereon with the noble metal nanoparticle layer of different localized plasmon resonance band; wherein when a light is launched into the optical fiber, a detecting unit is used to detect a localized plasmon resonance signal which is generated by the interaction between the noble metal nanoparticle layer and the light.

9. The localized plasmon resonance sensing device according to claim 8, wherein a normal plane of the each notch is formed by connecting an intersection line of the first sidewall and the second sidewall with a core axis of the optical fiber, and the normal planes are parallel with each other.

10. The localized plasmon resonance sensing device according to claim 8, wherein a normal plane of the each notch is formed by connecting an intersection line of the first sidewall and the second sidewall with a core axis of the optical fiber, and the each normal plane forms an included angle with an adjacent normal plane.

* * * * *

UNITED STATES PATENT AND TRADEMARK OFFICE
CERTIFICATE OF CORRECTION

PATENT NO. : 8,355,134 B2
APPLICATION NO. : 12/798056
DATED : January 15, 2013
INVENTOR(S) : Lai-Kwan Chau et al.

It is certified that error appears in the above-identified patent and that said Letters Patent is hereby corrected as shown below:

Title Page, Item (75) Inventors, the first name inventor should read "Lai-Kwan Chau". The patent currently presents the first name of the first inventor as "La-Kwan".

Signed and Sealed this
Twelfth Day of March, 2013

Teresa Stanek Rea
*Acting Director of the United States Patent and Trademark Office*